United States Patent
Livingston et al.

(10) Patent No.: US 6,986,881 B1
(45) Date of Patent: Jan. 17, 2006

(54) IDENTIFICATION OF COMPOUNDS THAT MODIFY TRANSCRIPTIONAL RESPONSES TO HYPOXIA

(75) Inventors: David M. Livingston, Brookline, MA (US); Andrew L. Kung, Roslindale, MA (US); Shoumo Bhattacharya, Oxford (GB)

(73) Assignee: Dana-Farber Cancer Institute, Inc., Boston, MA (US)

( * ) Notice: Subject to any disclaimer, the term of this patent is extended or adjusted under 35 U.S.C. 154(b) by 106 days.

(21) Appl. No.: 10/009,584

(22) PCT Filed: Jun. 2, 2000

(86) PCT No.: PCT/US00/15325

§ 371 (c)(1),
(2), (4) Date: May 21, 2002

(87) PCT Pub. No.: WO00/74725

PCT Pub. Date: Dec. 14, 2000

Related U.S. Application Data (60) Provisional application No. 60/137,625, filed on Jun. 4, 1999.

(51) Int. Cl.
*A61K 49/00* (2006.01)
*C12N 15/63* (2006.01)
*C12N 5/10* (2006.01)
*C12N 15/85* (2006.01)

(52) U.S. Cl. .................. 424/9.1; 424/9.2; 424/9.6; 435/320.1; 435/6; 435/7.1; 435/29

(58) Field of Classification Search ............... 435/6, 435/7.1, 29, 325, 320.1, 69.1, 455; 424/9.1, 424/9.2, 9.6
See application file for complete search history.

(56) References Cited

U.S. PATENT DOCUMENTS

| 5,658,784 A | | 8/1997 | Eckner et al. | |
|---|---|---|---|---|
| 6,165,977 A | * | 12/2000 | Mochly-Rosen | 514/16 |
| 6,436,654 B1 | * | 8/2002 | Berkenstam et al. | 435/7.8 |
| 2001/0034327 A1 | * | 10/2001 | Brunner et al. | 514/12 |

OTHER PUBLICATIONS

Arany et al., PNAS, 1996, vol. 93, pp. 12969-12973.*
Fandrey et al., Biochem. J., 1994, vol. 303, pp. 507-510.*
Arany et al. (1996). *Proc. Natl. Acad. Sci. USA* 93: 12969-12973.
Bhattacharya et al. (1999). *Genes and Development* 13: 64-75.
Ebert et al. (1998). *Mol. and Cell. Biol.* 18: 4089-4096.
Ema et al. (1999). *The EMBO J.* 18: 1905-1914.
Jiang et al. (1997). *J. of Biol. Chem.* 272: 19253-19260.
Kallio et al. (1998), *The EMBO J.* 17: 6573-6586.
Newton et al. (2000). *J. of Biol. Chem.* 275: 15128-15134.
Zhong et al. (2000). *Cancer Res.* 60: 1541-1545.

* cited by examiner

*Primary Examiner*—David Guzo
(74) *Attorney, Agent, or Firm*—Ivor R. Elrifi, Esq.; Cynthia A. Kozakiewicz, Esq.; Mintz, Levin, Cohn, Ferris, Glovsky and Popeo, P.C.

(57) ABSTRACT

The invention provides methods for identifying compounds that can be used to modify transcriptional responses to hypoxia, and use of such compounds in therapeutic and diagnostic methods.

8 Claims, 4 Drawing Sheets

IDENTIFICATION OF COMPOUNDS THAT MODIFY TRANSCRIPTIONAL RESPONSES TO HYPOXIA

This application claims priority to U.S. provisional application 60/137,625, filed Jun. 4, 1999.

STATEMENT AS TO FEDERALLY FUNDED RESEARCH

This work was supported, in part, by grants from the United States government (grants CA15751 and 5K08CA72993 from the National Institutes of Health). The government has certain rights in the invention.

BACKGROUND OF THE INVENTION

This invention relates to methods for identifying compounds that modify transcriptional responses to hypoxia.

As solid tumors evolve from a single malignant cell into a multicellular mass, oxygen tension in the tumor microenvironment drops as the passive diffusional capacity of the existing blood supply is surpassed (Nordsmark et al., Acta. Oncol. 33:383–389, 1994; Helmlinger et al., Nat. Med. 3:177–182, 1997; Adam et al., Head Neck 21:146–153, 1999). Tumor hypoxia decreases the efficacy of many common therapies (Brown, Mol. Med. Today 6:157–162, 2000), is a powerful stimulus for angiogenesis (Shweiki et al., Nature 359:843–845, 1992), and is linked to tumor progression (Zhong et al., Cancer Res. 59:5830–5835, 1999; Hockel et al., Cancer Res. 56:4509–4515, 1996) and metastasis (Brizel et al., Cancer Res. 56:941–943, 1996). Since chronic hypoxia differentiates tumor cells from their normal tissue counterparts (Zhong et al., Cancer Res. 59:5830–5835, 1999), therapeutic strategies have been developed that seek to exploit this difference by the design of drugs that are selectively activated under hypoxic conditions (Zeman et al., Int. J. Radiat. Oncol. Biol. Phys. 12:1239–1242, 1986) and hypoxia-induced gene therapy protocols (Binley et al., Gene Ther. 6:1721–1727, 1999; Shibata et al., Gene Ther. 7:493–498, 2000).

Cellular hypoxia triggers a multifaceted adaptive response that is primarily mediated by the heterodimeric transcription factor, HIF-1 (MacDonald et al., Mol. Cell. Biol. 13:5907–5917, 1993; Maltepe et al., Nature 386: 403–407, 1997). Under normoxic conditions, the alpha subunit (HIF-1α) is essentially undetectable due to its destruction by the ubiquitin-proteosome system (Salceda et al., J. Biol. Chem. 272:22642–22647, 1997; Huang et al., J. Biol. Chem. 271:32253–32259, 1996). This is achieved, in part, through targeting by the von Hippel-Lindau protein (Huang et al., J. Biol. Chem. 271:32253–32259, 1996). Under hypoxic conditions, through as yet unclear mechanisms, HIF-1α is stabilized and accumulates (Jiang et al., Am. J. Physiol. 271:C1172–1180, 1996). Stabilized HIF-1α heterodimerizes with its binding partner, ARNT (aryl hydrocarbon receptor nuclear translocator) (Wang et al., J. Biol. Chem. 270:1230–1237, 1995; Jiang et al., J. Biol. Chem. 271:17771–17778, 1996), a common binding partner of several βHLH-PAS domain proteins. The heterodimer interacts with p300/CBP (Arany et al., Proc. Natl. Acad. Sci. U.S.A. 93:12969–12973, 1996; Ebert et al., Mol. Cell. Biol. 18:4089–4096,1998; Kallio et al., EMBO J. 17:6573–6586, 1998; Carrero et al., Mol. Cell. Biol. 20:402–415, 2000) and SRC-1 family coactivators (Carrero et al., Mol. Cell. Biol. 20:402–415, 2000), binds to a cognate hypoxia-response element (HRE) (Jiang et al., J. Biol. Chem. 271:17771–17778, 1996), and thereby transactivates HRE-containing promoters and enhancers. Expression of HIF-1 target genes serves to maintain cellular homeostasis, at least in part, by promoting anaerobic glycolysis, facilitating erythropoiesis, and increasing blood delivery through vasodilatation and angiogenesis (Semenza, Annu. Rev. Cell. Dev. Biol. 15:551–578, 1999). The importance of the HIF-1 response pathway in human tumorigenesis is underscored by the finding that HIF-1α is overexpressed in multiple human cancers (Zhong et al., Cancer Res. 59:5830–5835, 1999).

Adaptation to hypoxic conditions not only plays a role in tumor progression, but is also important in conditions of local tissue hypoxia/anoxia, such as in the pathogenesis of myocardial ischemia and stroke. The HIF pathway has also been shown to be important in certain inflammatory conditions, such as Crohn's disease.

SUMMARY OF THE INVENTION

The invention provides a method of identifying a compound that modulates a transcriptional response to hypoxia in a cell (e.g., a cultured cell or a cell in an animal). In this method, a cell, or the extracellular environment of a cell, is contacted with a candidate compound. The cell is then subjected to hypoxic conditions, and a transcriptional response of the cell to the hypoxic conditions is assessed. In this method, the transcriptional response can be expression of a reporter gene under the control of a hypoxia-responsive promoter or an endogenous hypoxia-responsive gene. The reporter gene can be, for example, luciferase, green fluorescent protein, yellow fluorescent protein, or cyano-fluorescent protein. The endogenous gene can encode, for example, vascular endothelial growth factor, erythropoietin, heme oxygenase, iNOS, glucose transporter 1, glucose transporter 3, hexokinase, ALDA, or transferrin. The hypoxic conditions to which the cells are exposed can be by exposure to low oxygen levels, or induced chemically, e.g., by deferoxamine or cobalt chloride.

The invention also provides a method of identifying a compound that modulates a transcriptional response to hypoxia in a cell. This method involves providing a first transcription factor that is involved in a transcriptional response to hypoxia in a cell, or a fragment thereof; contacting the first transcription factor, or fragment thereof, with a candidate compound; and determining whether the candidate compound affects the interaction of the first transcription factor with a second transcription factor, or a fragment thereof.

Another method provided in the invention is a method of identifying a compound that modulates a transcriptional response to hypoxia in a cell. This method involves providing a first and a second transcription factor that are involved in a transcriptional response to hypoxia in a cell, or fragments thereof; contacting the first and second transcription factors, or fragments thereof, with a candidate compound; and determining whether the candidate compound affects the interaction of the first and second transcription factors.

In either of the two methods described immediately above, the first transcription factor can include a peptide of HIF-1α (e.g., the TAD-C region) and the second transcription factor can include peptide of p300/CBP (e.g., the CHI region, or, in particular, amino acids 302–418, amino acids 302–443, or amino acids 302–528 of p300/CBP). With both transcription factors, the peptide can include the regions listed above, or larger segments (e.g., entire proteins) including these regions.

The invention also provides a method of treating a condition characterized by hypoxia in a patient, hypoxia in a localized tissue, or activation of the HIF-1 pathway. This method involves administering to a patient a compound that modifies (decreases or increases) a transcriptional response to hypoxia in the patient. In the case of a compound that decreases the response, the method can be used to treat, for example, cancer or an inflammatory condition of abnormal neovascularization that is mediated by the hypoxia response pathway. In the case of a compound that increases the response, the method can be used to treat, for example, myocardial ischemia, stroke, or an erythropoietin deficiency. The compound can, e.g. bind to HIF-1α. The invention also includes the use of compounds identified according to the invention in the preparation of medicaments for treating diseases associated with hypoxia, such as those described herein.

Also included in the invention is a method of detecting a hypoxic tissue, cell, or tumor in a patient. This method involves administering to the patient a detectably labeled compound (e.g., a compound that binds to HIF-1α.) that modifies a transcriptional response to hypoxia in the patient.

The invention provides several advantages. For examples, compounds identified using the methods of the invention can be used as therapeutic molecules for preventing or treating conditions characterized by hypoxia. Thus, compounds that are found to decrease transcriptional responses to hypoxia by, e.g., disrupting the interaction between HIF-1α and p300/CBP, can be used in methods to treat cancer, resulting in decreased tumor angiogenesis, metabolic derangement, and tumor cell death. Compounds that increase transcriptional responses to hypoxia by, e.g., potentiating the interaction between HIF-1α and p300/CBP, can be used to treat conditions such as ischemic stroke and myocardial ischemia. Compounds identified according to the invention can also be used to treat inflammatory conditions, such as Crohn's disease, as well as erythropoietin deficiencies (e.g., as found in renal transplant patients). The invention also provides sensitive imaging reagents and methods.

Other features and advantages of the invention will be apparent from the following detailed description and the drawings.

DETAILED DESCRIPTION

Local tissue hypoxia is associated with many different disease states including certain tumors, myocardial ischemia, stroke, certain inflammatory processes, conditions of neovascularization, and certain polycythemic conditions. A multifaceted adaptive response to hypoxia is facilitated by the stabilization and accumulation of the alpha subunit of hypoxia inducible factor 1 (HIF-1). HIF-1α forms a complex with its binding partner, aryl hydrocarbon receptor nuclear translocator (ARNT), as well as the p300/CBP transcriptional coactivators. This complex induces the transcription of genes that serve to maintain cellular homeostasis in the face of hypoxic conditions. For example, the HIF-1/p300/CBP complex plays a role in inducing expression of genes such as those encoding erythropoietin, which leads to erythropoiesis; vascular endothelial cell growth factor (VEGF), which is a primary mediator of angiogenesis; iNOS and heme oxygenase, which play roles in vasodilation; and the glucose transporter and glycolytic enzymes, which play roles in anaerobic metabolism.

No tractable methods of attenuating the HIF-1 pathway have been previously described. We have now identified a way of disrupting hypoxia-inducible transcription by interfering with the interaction of HIF-1α a with p300/CBP. Specifically, we have identified a region in HIF-1α that interacts with the CH1 region of p300/CBP, and have shown that disruption of the interaction between these regions can block the transcriptional response to hypoxia in cells. The invention provides methods for identifying reagents or compounds (e.g., small molecules, peptides, proteins, antisense molecules, ribozymes, triple helices, and antibodies, or fragments thereof) that interfere with the HIF-1 pathway. The disruption can occur at any point in the pathway, for example, at the sensing by the cell of decreased oxygen tension, stabilization and accumulation of HIF-1α, binding of HIF-1α to ARNT and p300/CBP, binding of HIF-1α/ARNT/p300/CBP to hypoxia-responsive elements (HRE) of hypoxia-inducible genes, and transactivation of HRE-associated genes by HIF-1α/ARNT/p300/CBP. Reagents that block or disrupt this interaction can be used in methods to prevent hypoxia-induced gene expression, and, thus, for example, as anti-neoplastic therapeutics. Such reagents can also be used to treat inflammatory diseases, such as Crohn's disease, retinopathies, and polycythemia. Reagents that potentiate this interaction can be used, for example, in methods of treating ischemic stroke or myocardial ischemia.

Reagents that modify transcriptional responses to hypoxia, e.g., through disrupting the HIF-1α/p300/CBP CH1 interaction that is involved in cellular responses to hypoxia, can be identified using any of a number of standard methods, including in vitro, cell-based, and in vivo methods. Of particular interest are high throughput screening methods employing, for example, libraries contained on chips. Such methods are well known in the art, and can readily be adapted for use in the invention.

Specific examples of screening methods that can be used in the invention are as follows. For example, a fusion protein, such as a GST fusion protein, containing the portion p300/CBP that binds to HIF-1α (i.e., a peptide including the p300/CBP CH1 region (e.g., p300/CBP 302–418, p300/CBP 302–443, p300/CBP 302–528, or any fragment including amino acids 302–418, up to full length p300/CBP; see below)) can be produced in a bacterial system. A labeled (e.g., $S^{35}$-labeled), in vitro transcription/translation HIF-1α peptide (e.g., TAD-C or a peptide or polypeptide including TAD-C, up to full lenth HIF-1α; see below) can then be assayed for binding to the fusion protein. In a variation of this method, the HIF-1α peptide is made as a fusion protein, and binding of a labeled p300/CBP CH1 region-containing peptide is measured. Details of such an example of an in vitro binding assay that can be used in the invention are provided below (see Experimental Results and Materials and Methods, below).

An additional example of an in vitro method that can be used in the invention is an ELISA-based assay, in which GST-CH1 is expressed and purified from bacteria and a HIF polypeptide (e.g., a HIF peptide containing amino acids 786–826) is synthesized as a biotinylated synthetic peptide. The ELISA is set up by immobilizing the biotinylated HIF peptide on a strepatvidin coated plate. Candidate compounds are then added and, subsequently, GST-CH 1. After washing, the amount of bound GST-CH1 is assayed by using an enzyme-linked anti-GST antibody. The assay can be varied, for example, by immoblizing GST-CH1, adding the biotinylated HIF peptide, and detecting binding with enzyme linked strepavidin. Also, CH1 and the HIF polypeptides can be reversed in their roles in the assays described above, or could be alternatively tagged with other epitopes (e.g., HA, myc, or HIS6), and activity could be measured by enzymes linked to the appropriate antibody. Moreover, different binding partners in the pathway of hypoxia-induced transcription can be used in the methods described above. For example, HIF-1α and ARNT, or HIF and the hypoxia-response element of hypoxia-induced genes, can be used as target binding partners in these methods. Additional in vitro binding methods that can be used in the invention are known to those of skill in this art. The methods are carried out in the presence and absence of a candidate compound, and detection of a change in binding can be used as a read out for the identification of a compound that may be useful in modulating the cellular response to hypoxia in the invention. As is mentioned above, compounds that are found to disrupt or interfere with binding are candidates for treating conditions in which it is desirable to block the hypoxic response (e.g., neoplastic diseases; see above), while compounds that are found to increase binding are candidates for treating conditions in which it is desirable to potentiate the hypoxic response (e.g., myocardial ischemia and stroke). In addition, because HIF-1 is the primary regulator of erythropoietin production, compounds found to increase transcriptional responses to hypoxia may have utility in treating patients having conditions associated with a deficiency of erythropoietin, e.g., renal transplant patients and patients with anemia, of any etiology.

In addition to in vitro methods, such as those described above, any of a number of cell-based methods can be used to identify or characterize candidate compounds according to the invention. For example, cells can be subjected to hypoxic conditions in the presence or absence of a candidate compound, and differences in the hypoxic phenotype can be detected. For example, expression of a hypoxia-induced gene, such as VEGF or erythropoietin, can be measured (e.g., by RNAse protection, Northern blot analysis, quantitative RT-PCR, or real-time PCR), or cell death can be measured. Alternatively, cells can be transfected with a construct including a reporter gene (e.g., a luciferase, fluorescent protein, or β-galactosidase gene) and a hypoxia-responsive promoter (e.g., the erythropoietin promoter), and the effect of the compound on expression of the reporter gene can be measured. Additional cell-based methods are known to those of skill in this art, and use of these methods is included in the invention.

For example, a cell-based assay can be used to identify compounds that act at different points along the HIF pathway. Such an assay can involve use of a cell line having a stably integrated hypoxia-inducible reporter gene (e.g., luciferase, a fluorescent protein, or β-galactosidase gene) under the control of a hypoxia responsive promoter or enhancer element (e.g., VEGF or erythropoietin). Cells are plated in a multiwell format, candidate compounds are added, and then the cells are made hypoxic either by true hypoxia (e.g., 1% oxygen) or by adding deferoxamine or $CoCl_2$ to artificially activate the HIF pathway. Hypoxia-inducible transcription can then be read out by fluorescence or luciferase activity. In a variation of this method, a second fluorescent protein or Renilla luciferase can, in the same cell, be constitutively expressed under the control of another promoter as an internal standard. This allows control for non-specific suppression of transcription or non-specific cytotoxicity, which would result in decreased fluorescence of the constitutive marker, as well as the hypoxia-responsive marker. Again, this method has the advantage of identifying compounds that target p300/HIF-1α, but also can be used to identify compounds that target other nodes on the pathway (e.g., the ARNT/HIF-1α interaction, the HIF-1/DNA interaction, and HIF-1α stabilization). This assay could also identify compounds that up-regulate the hypoxia pathway. Such compounds may have utility in terms of being pro-angiogenic (e.g., for treating coronary artery disease, to increase EPO production, etc.).

For any two specific targets, a mammalian two hybrid-based assay can also be used. For example, one partner can be expressed fused to yellow fluorescent protein (e.g., YFP-CH1) and the other partner fused to cyano-fluorescent protein (e.g., CFP-HIF-1α). Cells are stably transfected to express these fusion proteins. The interaction of the proteins can be scored by FRET (fluorescence resonance energy transfer). Compounds that result in loss of FRET are identified as disrupting the protein—protein interaction. Alternatively, a cell can be engineered to express Gal4-CH1, HIF-VP16, and a Gal4-GFP reporter. Loss of GFP signal indicates identification of a compound that disrupts the mammalian two hybrid interaction between Gal4-CH1 and HIF-VP 16, with resulting decreased GFP expression off of the ectopic Gal4 promoter. These assays, relying on ectopically expressed proteins, do not necessarily require hypoxic conditions.

Another example of a cell-based assay involves linking a hypoxia-responsive element (HRE) to a potentially toxic gene product (e.g., HRE-TK), and then selecting for compounds that prevent cytotoxicity (e.g., with gancyclovir) under hypoxic conditions (real or chemically induced). Such an assay scores positive for compounds that inhibit hypoxia-inducible transcription and are in and of themselves not toxic.

All of the assays described above can be set up as high-throughput screens of libraries of natural and synthetic compounds. For example, libraries of compounds, such as peptides or proteins, that are immobilized on chips can be used. In addition, the cell-based assays are particularly amenable for use in screening for polypeptides or proteins that inhibit the hypoxia-response. Specifically, high titer/high complexity retroviral libraries have been constructed encoding for polypeptides, anti-sense RNA, or random peptides. Such retroviral libraries can be used to infect a stably integrated HRE-reporter cell and, by fluorescence-activated cell sorting, cells in which the hypoxia-response has been changed, for example, diminished or increased (e.g., as detected by changes in fluorescence), can be sorted out at a frequency of $1/100,000-1/1,000,000$. The sequence encoded by the integrated retrovirus can be determined by rescuing the insert using PCR. In addition, crystal or solution structures of components of the HIF pathway, fragments of these components, such as HIF polypeptides (e.g., TAD-C), p300/CBP (e.g., CH1), as well as p35srj, or complexes of these components, can be used in the identification of small molecules that mimic the 3D structures, using standard databases.

In addition to in vitro and cell-based methods, such as those described above, in vivo methods can be used to identify or characterize compounds according to the invention. One example of an in vivo method is a tumor implantation model, involving xenografts into nude mice. In such a method, tumor cells are implanted into nude mice, which are then either treated with a candidate compound or left untreated. The effect of a candidate compound can be determined, for example, by measuring tumor size or by postmortem histological analysis (e.g., analysis of levels of HIF-1α, VEGF, angiogenesis, and cell death). Additional tumor models are known in the art and can be used in the methods of the invention. As compounds become characterized as having a desired effect (e.g., decreasing tumor growth or angiogenesis), they can be analyzed for effects on models of specific types of cancers, in an effort to determine which types of human diseases may be treated using the compounds. In vivo methods can also be used to identify or characterize compounds that potentiate hypoxia-induced transcription, and thus are candidate compounds for treating myocardial ischemia or stroke.

In an additional in vivo method, tumor cells can be engineered to express luciferase, such cells can be implanted into mice, and luciferase activity can be detected in the live animal after tail vein injection of luciferin. Specifically, utilizing a sensitive CCD camera, photons can traverse through the skin of the animal and light emission can be detected and quantified in a non-invasive way. Animals can be followed longitudinally through time as this is a non-lethal technique. As an extension of such technology, we have engineered tumor cell lines that have luciferase driven by a hypoxia-responsive element (multimerized Epo enhancer HRE). Once injected into nude mice, the amount of tumor hypoxia can be quantified as tumors enlarge. At a given tumor volume, after quantifying hypoxia-inducible luciferase activity, compounds of interest can be injected. The hypoxia-specific reporter activity in tumor cells can then be serially followed, in the same animal, as treatment with the compound is continued. Any compound that specifically suppresses hypoxia-inducible transcription in vitro can thus be assayed for the ability to do so in vivo in an intact animal. Transgenic mice with a HRE-luciferase integrated in every cell have been made. Using such an animal, we can determine the effect of a given compound on any "normally" occurring local tissue hypoxia (e.g., whether there is any basal hypoxia-inducible transcription in highly oxygen dependent organs, such as brain and kidneys, and how the candidate compounds effect this activity). As a further extension, HRE-*Renilla* luciferase integrated tumor cell lines can be used. Such tumor cell lines are implanted into HRE-luciferase transgenic mice, so that tumor cell hypoxia and host animal hypoxia can be separately measured. Such a system can be used to titrate compound doses to achieve a therapeutic index, in which tumor cell hypoxia-inducible transcription was reduced, but not normal tissue activity.

In addition to the screening methods described above, standard methods for preparing peptide mimetics can be carried out to obtain molecules that modify transcriptional responses to hypoxia, e.g., by disrupting the interaction between HIF-1α and p300/CBP. In addition to small molecule modifiers that affect, e.g., the interaction between HIF-1α and CH1, peptide molecules can be identified. For example, phage display can be used to optimize or identify peptide ligands of the CHI and HIF-1α binding domains. Compounds identified using these methods can be tested using the in vitro, cell-based, and in vivo systems described above.

p35srj is a protein that has a negative regulatory function on the HIF-1 pathway (Bhattacharya et al., Genes Dev. 13(1):64–75, 1999). It interferes with this pathway by binding to p300/CBP and inhibits HIF-1 transactivation by blocking the HIF-1α/p300 CH1 interaction. P35srj can thus be used in the invention as a prototype protein that interferes with the HIF-1 pathway.

Compounds identified using the methods of the invention can be administered to patients in need of treatment (e.g., patients having cancer, any of the other diseases listed above, or any other disease or condition associated with hypoxia) using standard modes of administration, such as by oral, intravenous, subcutaneous, intramuscular, and parenteral administration. Appropriate dosages of compounds identified using the methods of the invention can be readily determined by one of skill in the art, and can be, for example, 0.001–50 mg/kg/patient. In addition, peptide-based compounds can be administered using gene therapy methods.

Compounds identified using the methods of the invention can also be used in imaging methods. As is discussed above, HIF-1 is unstable under normoxic conditions, and thus normal cells do not contain detectable levels of HIF-1α. Compounds that are identified as binding to HIF-1α, according to the invention, thus can be labeled for use in high resolution imaging methods to detect cancer cells and tumors, as well as ischemic tissue resulting from, e.g., stroke or heart disease.

The methods of the invention are based, in part, on the following experimental results.

Experimental Results

Figure 1A:
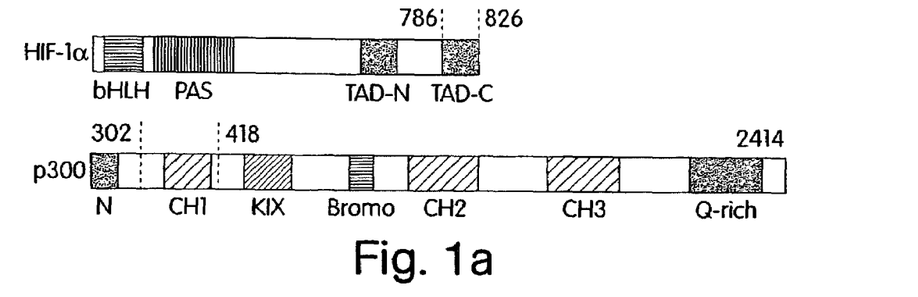
FIG. 1A is a schematic representation of HIF-1αa and p300. The amino acid numbers indicated for each protein define the boundaries of the minimal interaction domains.
Figure 1B:
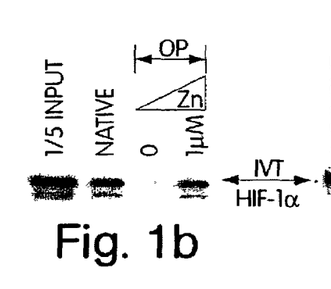
FIG. 1B shows that zinc is required for the interaction of GST-CH1 with HIF-1α. GST-CH1 (amino acids 302–528) was assayed for its ability to bind to in vitro translated (IVT) full length HIF-1α either in its native state after purification from bacteria or after washing with 1,10-phenanthroline (OP), a heavy metal chelator. The addition of 1 μM zinc sulfate after chelation restored binding activity.
Figure 1C:
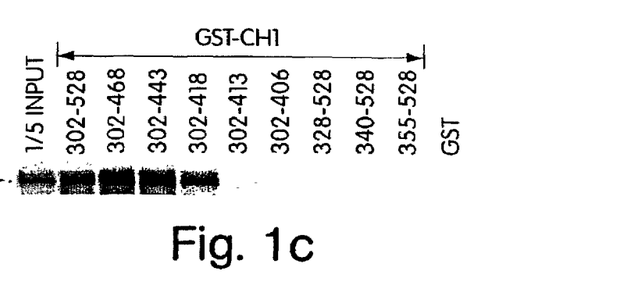
FIG. 1C shows the results of assays of carboxy- and amino-terminal truncation mutants of GST-CH1, with amino acid boundaries as indicated, for their ability to pull down full length IVT HIF-1α.
Figure 1D:
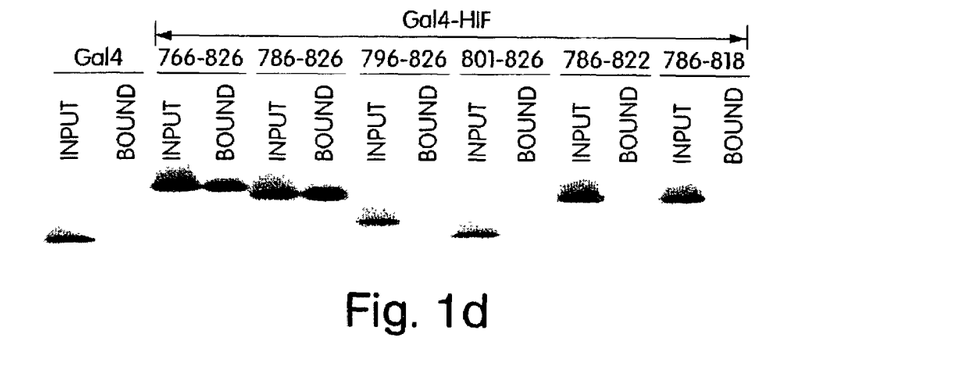
FIG. 1D shows the results of binding assays of the indicated truncation mutants of the carboxy-terminus of HIF-1α, constructed as fusions to Gal4 and translated in vitro, using GST-CHI (amino acids 302–443). One fifth of the total IVT product used for each binding assay is indicated (Input), along with the amount bound by GST-CH1 (Bound).

The detailed structural requirements for p300/CBP binding to HIF-1α were mapped by in vitro assays utilizing a series of GST-fused deletion mutants centered around the CH1 domain of p300, the primary HIF-1α interacting unit of that protein (Arany et al., Proc. Natl. Acad. Sci. U.S.A. 93:12969–12973, 1996; Kallio et al., EMBO J. 17:6573–6586, 1998). These mutant fusion proteins were assayed for binding to full length, iii vitro translated HIF-1α a zinc-dependent process (FIG. 1B). The minimal HIF-1α binding domain proved to encompass 116 residues (amino acids 302–418 of p300), which includes the CH1 domain and some flanking sequences (FIGS. 1A and 1C). To map the minimal p300-binding domain of HIF-1α, a series of Gal4-fused truncation mutants of the C-terminus were generated. These Gal4 fusion proteins were translated in vitro and probed for their ability to bind to GST-CH 1 (amino acids 302–443). The C-terminal 41 residues of HIF-1α, the so called C-terminal transactivation (TAD-C) domain (Jiang et al., J. Biol. Chem. 272:19253–19260, 1997) were found to be necessary and sufficient for binding to GST-CH1α (FIGS. 1A and 1D).

Figure 1E:
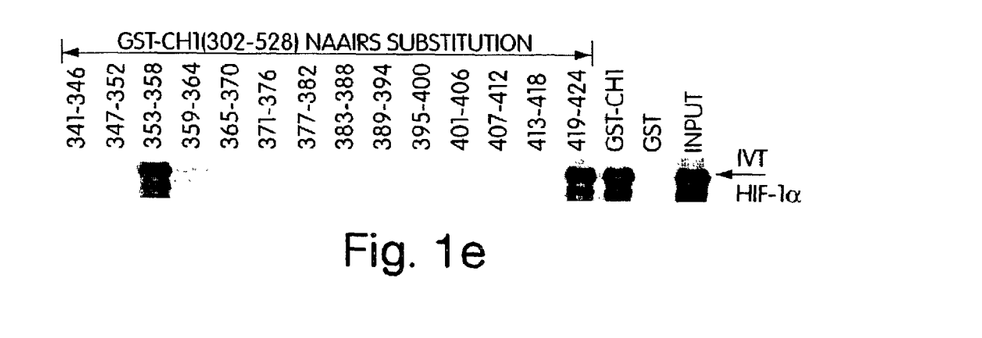
FIG. 1E shows the results of assays of the ability of serial substitution mutants of GST-CH 1 (amino acids 302–528) produced as GST fusion proteins, with the sequence NAAIRS (SEQ ID NO: 1) inserted in place of the indicated amino acids, to bind to IVT full length HIF-1α.

To study further the requirements for HIF-1α/CH I binding, a series of GST-CH1 (amino acids 302–528) internal substitution mutants were generated. These serial, non-overlapping mutants spanned residues 341–424 of p300. In each mutant, five residues were deleted and the sequence, Asp-Ala-Ala-Ile-Arg-Ser (NAAIRS, SEQ ID NO: 1), inserted. The NAAIRS sequence can assume an α-helical or β-strand conformation (Wilson et al., Proc. Natl. Acad. Sci. U.S.A. 82:5255–5259, 1985), thus, decreasing the likelihood of generalized conformational disruption following the deletion/insertion event. Almost all substitutions abolished CH I binding to full length HIF-1α (FIG. 1E), suggesting that the CH1 domain must assume a complex, zinc-coordinated conformation in order to interact with HIF-1α.

Figure 2A:
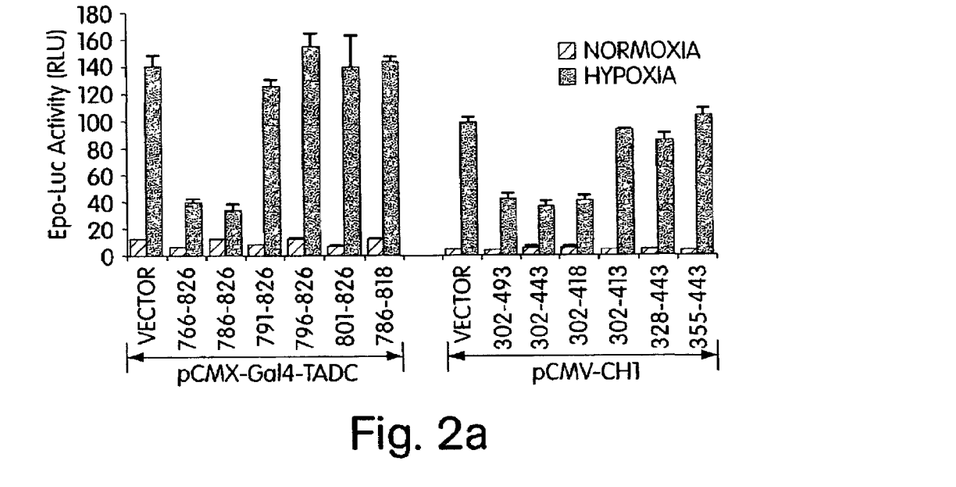
FIG. 2A is a graph showing the results of luciferase and β-galactosidase assays, in which Hep3B cells were cotransfected with an Epo-luciferase reporter (100 ng), pCMV-LacZ (100 ng), and the indicated expression plasmids (300 ng). Cells were subsequently exposed to either ambient (Normoxia, stippled bars) or 1% (Hypoxia, solid bars) oxygen for 18 hours prior to assay. The results are expressed as corrected relative light units (RLU, mean of three independent transfections ±S.D.).

Overproduction of polypeptides corresponding to these minimal binding domains (TAD-C or CH1) led to attenuation of hypoxia-inducible reporter activity (FIG. 2A). Moreover, only those TAD-C and CH1 mutants that bound to an intact target in vitro (FIGS. 1C and 1D) had a dominant-negative effect on hypoxia-inducible reporter activity in vivo (FIG. 2A). In titration experiments, it appeared that TAD-C polypeptides were more potent suppressors of HIF function than were CH1-containing dominant-negative polypeptides, perhaps because of the imputed conformational complexity of CH1. Accordingly, subsequent experiments focused on the activity of a wild type TAD-C polypeptide (amino acids 786–826 of HIF-1α) compared to that of an eight residue truncated mutant (amino acids 786–818 of HIF-1 a, which was unable to bind to GST-CH1 (FIG. 1D) and which failed to exert a dominant-negative effect on hypoxia-inducible reporter activity (FIG. 2A).

Figure 2B:
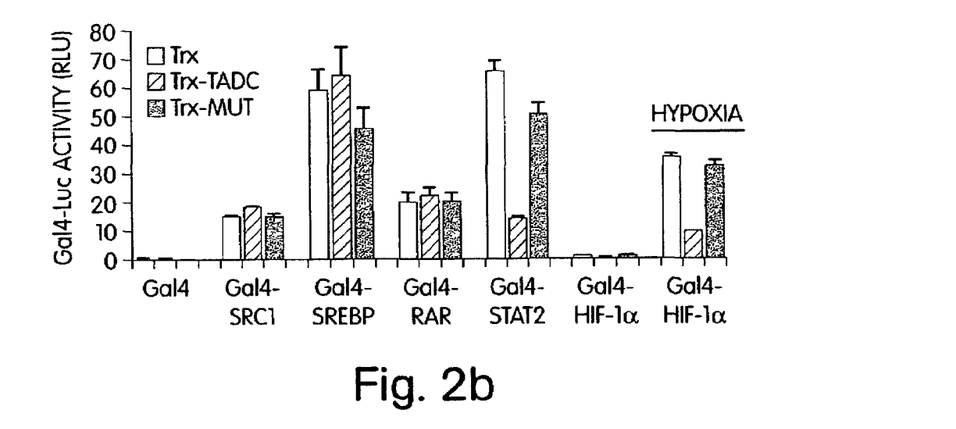
FIG. 2B is a graph showing the effect of TAD-C expression on p300/CBP dependent transactivation. Hep3B cells were cotransfected with the indicated thioredoxin-constrained fusion protein expression plasmids (300 ng), the indicated Gal4-fusion proteins (20 ng), Gal4-luciferase reporter (100 ng), and pCMV-LacZ (50 ng). Where indicated, cells were exposed to hypoxia for 18 hours. The results are expressed as corrected RLU (mean of three independent transfections ±S.D.).

By comparison with its effects on HIF-1α-mediated transcriptional activity, TAD-C polypeptide overexpression had no effect on RAR, SREBP2, or SRC-1, which interact with the N-terminal (Chakravarti et al., Nature 383:99–103, 1996), KIX (Oliner et al., Genes Dev. 10:2903–2911, 1996) and the glutamine-rich (Yao et al., Proc. Natl. Acad. Sci. U.S.A. 93:10626–10631, 1996) domains of p300/CBP respectively (FIG. 2B). However, it did inhibit the transcriptional activity of STAT2, which, like HIF-1α, uses CH1 to mediate its coactivation (Arany et al., Proc. Natl. Acad. Sci. U.S.A. 93:12969–12973, 1996; Bhattacharya et al., Nature 383:344–347, 1996). These results imply that an intact TAD-C polypeptide binds and blocks access of multiple proteins to the CH1 domain, without inducing a generalized suppressive effect on other p300/CBP functions.

Figure 2C:
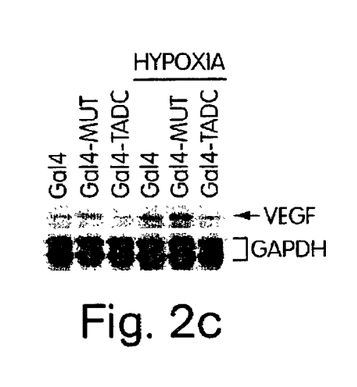
FIG. 2C shows the results of a ribonuclease protection assay that was conducted to determine VEGF and GAPDH mRNA abundance. In this assay, HepG2 cells were infected at an MOI of 10 with retroviruses encoding Gal4 alone or Gal4 fused with wild type or mutant (MUT) TAD-C polypeptide. Cells were exposed to either ambient or 1% (Hypoxia) oxygen for 18 hours prior to preparation of total RNA.

To facilitate expression of the relevant TAD-C and mutant polypeptides, VSV-G pseudotyped retroviruses were engineered to express Gal14 carrier protein alone or Gal4 fused to either wild type or mutant TAD-C polypeptide. HepG2 cells were infected with these retroviruses at a multiplicity of infection (MOI) of 10, exposed to either normal or hypoxic conditions, and VEGF mRNA levels were determined by a ribonuclease protection assay. Equivalent expression of Gal4 and the Gal4 fused polypeptides was regularly achieved in this and related experiments (for example, see FIG. 3A, inset). Concordant with the reporter assays, noted above, VEGF mRNA abundance was reproducibly diminished in cells expressing wild type but not mutant TAD-C polypeptide, both under normoxic as well as hypoxic conditions (FIG. 2C). The overall abundance of HIF-1α under hypoxic conditions was not altered by introduction of TAD-C.

Figure 2D:
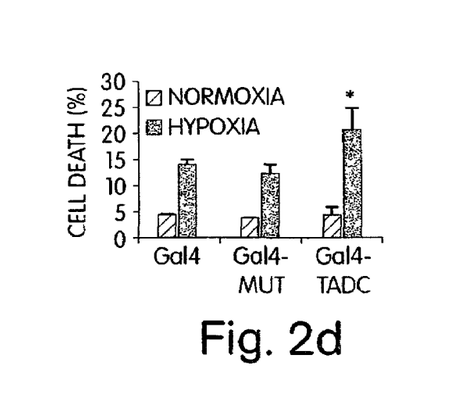
FIG. 2D is a graph showing the levels of cell death in an experiment in which HepG2 cells were infected at an MOI of 5 with retrovirus encoding the indicated Gal4 fusion proteins. Cells were exposed to either ambient or 1% oxygen for 36 hours, and then assayed for cell death by flow cytometric analysis using Annexin V staining and vital dye exclusion. The results are expressed as the mean of three independent experiments ±S.E.M. The asterisk denotes statistical significance (p=0.05) in comparison to controls.

Cell survival under normoxic conditions was essentially the same in HepG2 cells expressing either Gal4 alone or Gal4 fused to TAD-C or mutant polypeptide (FIG. 2D). Cell growth was also not affected under normoxic conditions. Under hypoxic conditions, however, cell death was slightly, but significantly, increased in cells expressing wild type TAD-C polypeptide, in comparison to cells expressing Gal4 alone or Gal4 fused with mutant polypeptide (FIG. 2D).

Figure 3A:
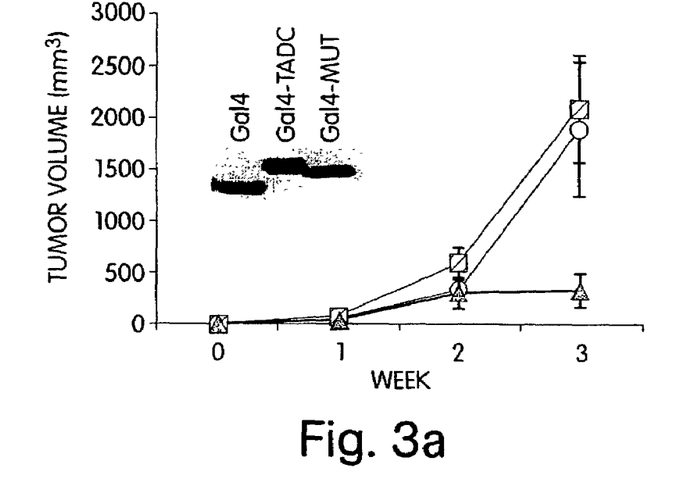
FIG. 3A is a graph showing the in vivo effect of TADC expression. HCT116 cells were infected at an MOI of 5 with retroviruses encoding Gal4 alone (circle), Gal4 fused with mutant TAD-C polypeptide (Gal4-MUT, square) or with wild type TAD-C polypeptide (triangle). A total of $4 \times 10^6$ cells were implanted subcutaneously into nude mice. The results are expressed as the mean ±S.D. of 8–10 independent tumors. The inset shows an immunoblot for Gal4 in infected cells, demonstrating equivalent levels of expression.
Figure 3B:
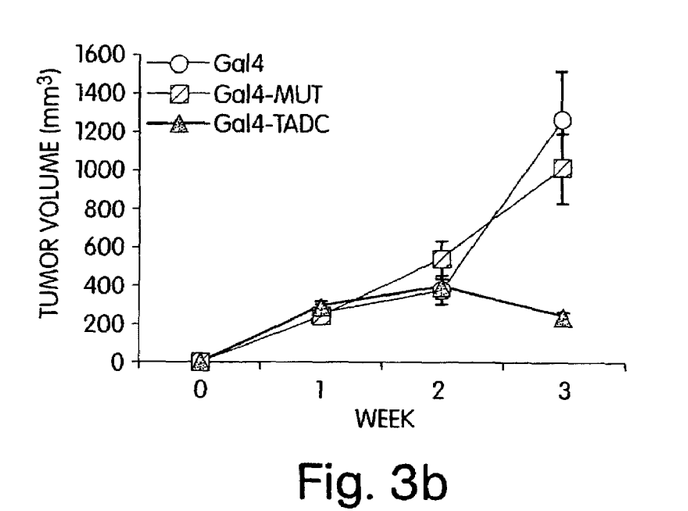
FIG. 3B is a graph showing results of the experiments described in reference to FIG. 3A for MDA-MB435S cells.
Figure 3C:
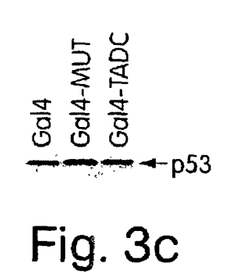
FIG. 3C is an immunoblot for p53 in HCT116 cells infected with the indicated retroviruses at an MOI of 10.

To extend these findings, the growth of modified human tumor cells was assayed in a nude mouse xenograft model. Tumor cells were retrovirally transduced at an equal MOI, resulting in equivalent expression of Gal4, or Gal4 fused to wild type or mutant TAD-C polypeptide (FIG. 3A, inset). Tumor growth was significantly and reproducibly attenuated in HCT116 (FIG. 3A) or MDA-MB435S (FIG. 3B) cells expressing wild type TAD-C polypeptide when compared to the same cells expressing Gal4 alone or Gal4 fused to mutant polypeptide (FIGS. 3A and 3B). This effect was independent of p53 status, since HCT116 cells have wild type p53, while MDA-MD435S cells express mutant p53. Furthermore, immunoblot analysis for p53 demonstrated no difference in p53 abundance in HCT116 cells expressing these three ectopic Gal4 polypeptides (FIG. 3C).

Figure 3D:
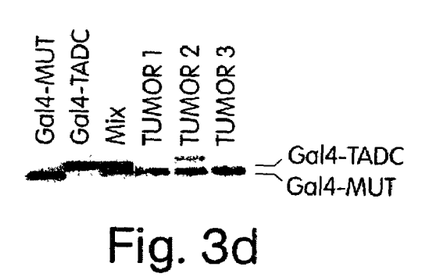
FIG. 3D is an immunoblot for Gal4, in an experiment in which HCT116 cells were infected with Gal4-MUT or Gal4-TADC at an MOI of 5. Cells were then mixed in equal proportion, and $6 \times 10^6$ cells were implanted into nude mice. After three weeks, tumors were excised (Tumor 1–3), and protein extracts were analyzed by immunoblotting for Gal4, along with extracts prepared from cells prior to implantation (Mix).

We were interested in learning whether the anti-tumor effect of TAD-C polypeptide expression was due to a paracrine effect, where a cell producing TAD-C elaborates a factor(s) which suppresses growth of surrounding tumor cells. Specifically, tumor cells expressing either Gal4-TAD-C or Gal4-mutant polypeptide were mixed in equal numbers prior to implantation. When tumors were excised after three weeks of growth, there was a strong bias towards cells expressing the mutant polypeptide (FIG. 3D), suggesting that the anti-tumor effect of expressing TAD-C was not a result of a paracrine effect arising from the elaboration of a trans-dominant anti-tumor factor.

Figure 4A:
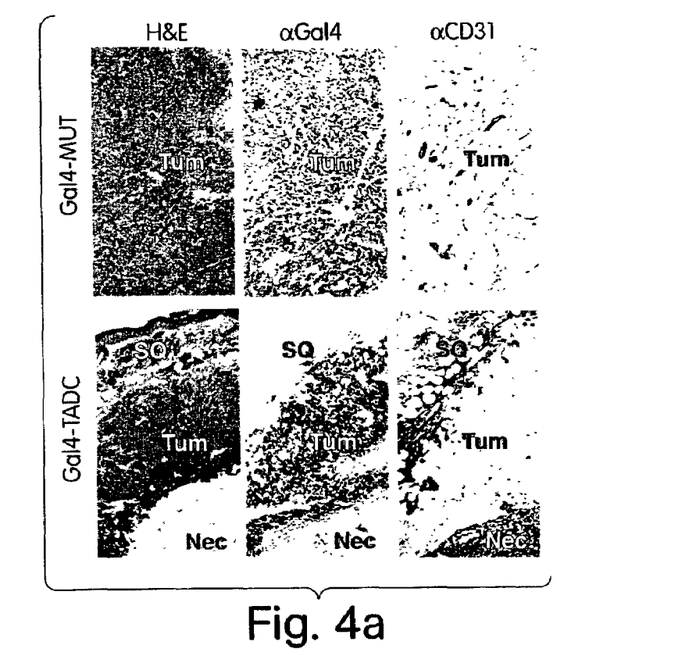
FIGS. 4A and 4B are a series of photographs showing that the in vivo effect of TAD-C expression can be rescued by a CH1-independent HIF-1α allele. Tumors arising from HCT116 cells infected with retrovirus encoding Gal4 fused with mutant (MUT) or wild type TAD-C polypeptide at an MOI of 5 were excised after 3 weeks of growth. Paraffin sections were stained with H&E or immunostained for Gal4 or CD31/PECAM. The subcutaneous tissue (SQ), tumor (Tum), and necrotic areas (Nec) are indicated.
Figure 4B:
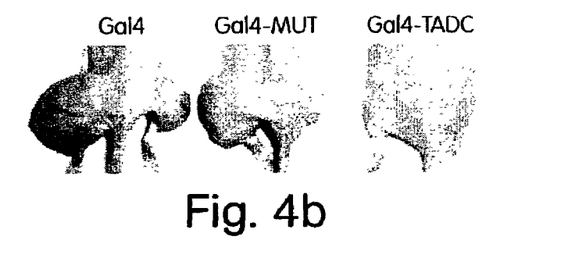
Figure 4C:
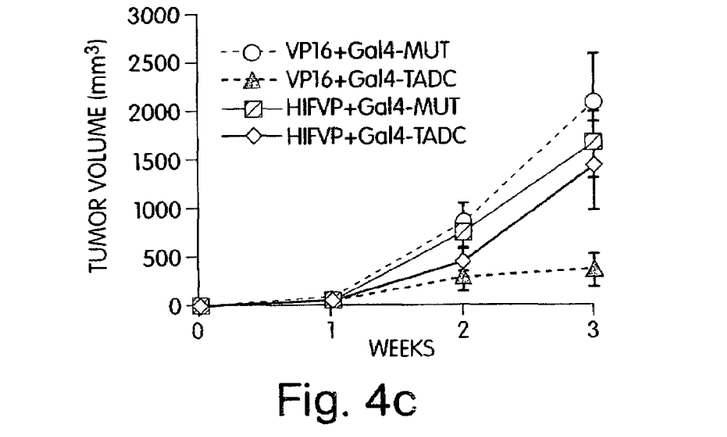
FIG. 4C is a graph showing the results of experiments in which HCT116 cells were infected with either pBABE-puro-VP16 (VP16) or pBABE-puro-HIF-VP16 (HIFVP), and selected with puromycin. These cells were then infected with retrovirus encoding either Gal4-MUT or Gal4-TADC at an MOI of 5. A total of $6 \times 10^6$ cells were implanted in nude mice. Results are the mean of 8 independent tumors ±S.D.

Necropsy and histological examination of the injection site of tumor cells engineered to express Gal4 fused TAD-C polypeptide revealed large areas of central necrosis with a small rim of viable tumor cells adjacent to the subcutaneous tissue (FIG. 4A), even in the absence of grossly measurable tumor at these sites (FIG. 4B). Control tumors arising from cells expressing Gal4 or Gal4 fused to mutant polypeptide revealed small areas of necrosis, but vast areas of viable tumor (FIG. 4A) were grossly palpable (FIG. 4B). Immunostaining for the endothelial cell marker, CD31/PECAM, revealed abundant capillary formation within control tumor segments compared to TAD-C expressing tumors (FIG. 4A). It is unclear whether this was a primary or secondary effect, i.e., that there were fewer tumor cells because of diminished vessel density, or vice versa.

Since several, known transcription factors interact with the CH1 domain of p300, and TAD-C polypeptide expression appears to generally disrupt CH1 function (FIG. 2B), we asked whether interference with HIF-1α binding/function is a critical component of the TAD-C anti-tumor effect. Accordingly, a HIF-1α allele was engineered in which the oxygen-degradation domain was deleted, and TAD-C was replaced with VP16 (HIF-VP16), creating a constitutively active, CH1-independent HIF-1α molecule. HCT116 cells were first transduced with either VP16 alone or with HIF-VP16. After selection, these cells were transduced with Gal4 fused to wild type or mutant TAD-C polypeptide. With coexpression of unfused VP16, tumor growth was attenuated by TAD-C in comparison to the mutant polypeptide (FIG. 5B), in agreement with the results summarized above. However, with coexpression of HIF-VP16, there was identical tumor growth by cells coexpressing either TAD-C or mutant polypeptide (FIG. 5B). By immunoblot analysis, coexpression of HIF-VP16 had no effect on expression of TAD-C or mutant polypeptide in comparison to coexpression of VP16 alone. Thus, other effects notwithstanding, disrupting the interaction of HIF-1α with CH1 is a necessary event in TAD-C mediated tumor growth suppression.

The experimental results described above were obtained using the following materials and methods.

Materials and Methods

Plasmids and Retroviruses. Plasmids were generated using standard techniques (Ausubel et al., Eds., *Current Protocols in Molecular Biology* (Wiley-Interscience, New York, 1988)) and were verified by sequencing. All mammalian expression vectors utilized CMV promoters. GST fusion proteins were generated by subcloning PCR fragments into pGEX vectors (Pharmacia). Gal4-fusion proteins were made in pCMX-Gal4(N) (R. Evans). Scanning NAAIRS mutagenesis of GST-CH1(amino acids 302–528) was performed using single strand mutagenesis (Muta-Gene, Bio-Rad) according to manufacturer's instructions. pCMV-CH1 mutants were constructed by subcloning PCR products in pCMV/myc/nuc (Invitrogen). A thioredoxin-constrained expression vector was created by subcloning PCR fragments of *E. coli* thioredoxin A into pcDNA3.1 (Invitrogen), creating new unique restrictions sites within the active loop similar to prior reports (LaVallie et al., Biotechnology (NY) 11:187–193, 1993). The HIF-1α plasmid used for in vitro translation, Epo-luciferase reporter, Gal4-luciferase reporter, and pCMV-LacZ, Gal4-SRC1, Gal4-SREBP2, Gal4-RAR, Gal4-STAT2, and Gal4-HIF1α expression vectors have been described previously (Arany et al., Proc. Natl. Acad. Sci. U.S.A. 93:12969–12973, 1996; Yao et al., Proc. Natl. Acad. Sci. U.S.A. 93:10626–10631, 1996; Bhattacharya et al., Nature 383:344–347, 1996; Bhattacharya et al., Genes Dev. 13:64–75, 1999). VSV-G pseudotyped retroviruses were constructed in pMMP, and packaged by cotransfection with pMD-MLV and pMD-G (R. Mulligan) in 293T cells. Titers were determined by infection of the intended target cell line. HIF-VP16 and VP16 retroviruses were constructed in pBABE-puro, and packaged and titered, as noted above.

In vitro translation and in vitro protein binding assays. Except where noted, all reagents were from Sigma. In vitro transcription/translation (IVT) was performed in the presence of $^{35}$S-methionine (NEN) using T3 or T7 polymerase coupled with rabbit reticulocyte lysates (TNT, Promega) according to the manufacturer's instructions. GST fusion proteins were produced in, and purified from, bacteria, and binding of IVT proteins was performed as previously described (Grossman et al., Mol. Cell. 2:405–415, 1998). Except where indicated, binding and wash buffer consisted of 20 mM Tris-HCl (pH 8.0), 150 mM NaCl, 0.2% NP-40, 1 mM DTT, 10 μM ZnCl$_2$, 2 μM EDTA, PMSF 50 μg/ml, pepstatin 1 μg/ml, leupeptin 1 μg/ml, and aprotinin 1.9 μg/ml. Where indicated, heavy metals were chelated by three changes of wash buffer containing 1,10-phenanthroline (Aldrich) at 10 mM. Zinc reconstitution after chelation of heavy metals utilized ultrapure zinc chloride (>99.999%, Aldrich).

Reporter assays. Luciferase and β-galactosidase assays were performed as previously described (Bhattacharya et al., Genes Dev. 13:64–75, 1999). In all cases, luciferase activity was corrected for β-galactosidase activity as an internal control for transfection efficiency and global changes in transcriptional activity. Results are expressed as corrected relative light units (RLU). For each reporter experiment, at least two independent experiments were performed.

Hypoxia. Hypoxia was achieved by incubating cells in a humidified environment at 37° C. in a Cellstar three gas incubator (Harris) maintained at 10% $CO_2$ and 1% $O_2$. Accurate $O_2$ and $CO_2$ regulation was periodically verified with a Fryrite gas analyzer (Bacharach).

Cell culture and retroviral infection. Tumor cell lines were obtained from the ATCC, and were cultured in DMEM supplemented with 10% FBS, penicillin, streptomycin, and L-glutamine (Gibco-BRL). Cells in logarithmic growth phase were serially infected 12 hours apart with VSV-G pseudotyped pMMP-Gal4 retroviruses to achieve a final MOI of 5 or 10, depending on the experiment. No selection was used, since immunostaining routinely demonstrated 100% infection of cells at these MOI. For pBABE-puro-VP16 or pBABE-puro-HIF-VP16, cells were infected at an MOI of <1 and selected with puromycin (2 µg/ml) for 4 days. Cells were allowed to recover for 1 day and then infected at an MOI of 5 with pMMP-Gal4 retroviruses.

Immunoblot, ribonzuclease protection, and cell death assays. Immunoblot analyses for Gal4 ($RK5C_1$, Santa Cruz Biotechnology), p53 (DO-1, Oncogene Research), and HIF-1α (OZ15 (Arany et al., Proc. Natl. Acad. Sci. U.S.A. 93:12969–12973, 1996)) were performed using standard techniques (Ausubel et al., Eds., *Current Protocols in Molecular Biology* (Wiley-Interscience, New York, 1988)). Total RNA was isolated (RNeasy, Qiagen), and ribonuclease protection assays performed utilizing a multiprobe human angiogenesis kit (RiboQuant, Pharmingen) according to the manufacturer's instructions. Cell death was measured by staining with anti-Annexin V antibody (Pharmingen) and 7-amino-actinomycin D (Pharmingen), and analyzed by flow cytometry according to the manufacturer's instructions.

Xenograft tumor model. Nude mice (Taconic) were obtained at 6–8 weeks of age and allowed to acclimate for 1 week prior to tumor implantation. Tumor cells were allowed to recover for at least 48 hours after retroviral infection prior to implantation into nude mice. The indicated number of tumor cells was injected subcutaneously and bilaterally into the flanks of mice. Tumors were measured with calipers, and tumor volume was calculated as $0.5 \times L \times W^2$. For each cell line, at least two independent experiments were performed. Where indicated, tumors were excised and fixed in 4% paraformaldehyde in phosphate buffered saline or minced and lysed in RIPA/300 buffer (50 mM Tris-HCl (pH 8.0), 300 mM NaCl, 1% NP40, 0.5% DOC, 0.1% SDS, 1 mM DTT, protease inhibitors). Immunostaining with anti-Gal 4 (IKE, Santa Cruz Biotechnology) or anti-CD31 (MEC13.3, Pharmingen) was performed using the Vectastain ABC Elite system (Vector) according to the manufacturer's instructions.

All references cited herein are incorporated by reference. Other embodiments are within the following claims.

What is claimed is:

1. An in vivo method of identifying a compound that modulates a transcriptional response to hypoxia, said method comprising:
   contacting a cell in vivo, or the extracellular environment of a cell in vivo, with a candidate compound;
   subjecting the cell in vivo to hypoxic conditions; and
   assessing a transcriptional response of the cell to the hypoxic conditions, wherein an increase or decrease in the transcriptional response to hypoxia in the cell in the presence of the candidate compound compared to the transcriptional response to hypoxia in a cell in the absence of the candidate compound indicates that the candidate compound modulates the transcriptional response to hypoxia.

2. The method of claim 1, wherein the transcriptional response is expression of a reporter gene under the control of a hypoxia-responsive promoter or an endogenous hypoxia-responsive gene.

3. The method of claim 1, wherein the cell is in a mammal.

4. The method of claim 1, wherein the hypoxic conditions to which the cells are exposed are induced by deferoxamine or cobalt chloride.

5. The method of claim 1, wherein said candidate compound is a peptide.

6. The method of claim 1, wherein said candidate compound is a small molecule.

7. The method of claim 2, wherein the reporter gene encodes luciferase, green fluorescent protein, yellow fluorescent protein, or cyano-fluorescent protein.

8. The method of claim 2, wherein the endogenous gene encodes vascular endothelial growth factor, erythropoietin, heme oxygenase, inducible nitric oxide synthase (iNOS), glucose transporter 1, glucose transporter 3, hexokinase, aldolase A (ALDA), or transferrin.

* * * * *

SEQUENCE LISTING

<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:consensus
      sequence

<400> SEQUENCE: 1

Asn Ala Ala Ile Arg Ser
 1               5